United States Patent
Barker et al.

(10) Patent No.: US 8,002,779 B2
(45) Date of Patent: Aug. 23, 2011

(54) DERMATOME BLADE ASSEMBLY

(75) Inventors: Douglas C. Barker, Canton, OH (US); David J. Boles, Copley, OH (US)

(73) Assignee: Zimmer Surgical, Inc., Dover, OH (US)

( * ) Notice: Subject to any disclaimer, the term of this patent is extended or adjusted under 35 U.S.C. 154(b) by 90 days.

(21) Appl. No.: 11/955,717

(22) Filed: Dec. 13, 2007

(65) Prior Publication Data

US 2009/0157095 A1    Jun. 18, 2009

(51) Int. Cl.
*A61B 17/50* (2006.01)
(52) U.S. Cl. .................................................. 606/132
(58) Field of Classification Search ............... 606/131, 606/132, 161, 166, 167, 171, 172; 30/208, 30/223, 167, 169, 288, 329, 337, 340, 339, 30/51, 53; 15/236.01, 236.08, 245.1; 407/99, 407/43, 42, 66; 125/16.01
See application file for complete search history.

(56) References Cited

U.S. PATENT DOCUMENTS

| | | | |
|---|---|---|---|
| 1,935,605 A | | 11/1933 | Atruda |
| 2,288,709 A | | 7/1942 | Hood |
| 2,419,114 A | * | 4/1947 | Briegel ..................... 606/132 |
| 2,435,278 A | | 2/1948 | Hood |
| 2,457,772 A | * | 12/1948 | Milford et al. .............. 606/132 |
| 2,691,377 A | * | 10/1954 | Hood ....................... 606/132 |
| 2,960,769 A | * | 11/1960 | Matwijcow ................. 30/340 |
| 3,327,711 A | | 6/1967 | Vallis |
| 3,412,732 A | * | 11/1968 | Simon ...................... 606/132 |
| 3,428,045 A | * | 2/1969 | Kratzsch et al. ............ 606/132 |
| 3,583,403 A | | 6/1971 | Pohl et al. |
| 3,670,734 A | * | 6/1972 | Hardy, Jr. .................. 606/132 |
| 3,820,543 A | * | 6/1974 | Vanjushin et al. ............ 606/132 |
| 3,857,178 A | * | 12/1974 | Stevens, II .................. 30/344 |
| 3,934,591 A | | 1/1976 | Gleason |
| 4,038,986 A | | 8/1977 | Mahler |
| 4,240,432 A | | 12/1980 | Mormann et al. |
| 4,270,540 A | | 6/1981 | Schwartz |
| 4,690,139 A | | 9/1987 | Rosenberg |
| 4,754,756 A | | 7/1988 | Shelanski |
| 4,838,284 A | | 6/1989 | Shelanski |
| 4,917,086 A | * | 4/1990 | Feltovich et al. ............ 606/132 |

(Continued)

FOREIGN PATENT DOCUMENTS

DE    1566041    4/1970

(Continued)

OTHER PUBLICATIONS

International Search Report from related PCT/US2008/086063; dated Jun. 12, 2009; 13 pages.

*Primary Examiner* — Tom Hughes
*Assistant Examiner* — David Eastwood
(74) *Attorney, Agent, or Firm* — Seager, Tufte & Wickhem LLC

(57) ABSTRACT

A dermatome has a main body with a first profile and at least one blade assembly with a blade, a size, an orientation corresponding to the main body, and a second profile. The second profile has characteristics corresponding to the first profile to properly orient and locate the at least one blade for proper mounting of the blade to the main body. The profiles are shaped to provide clearance for the second profile to reciprocate relative to the first profile.

15 Claims, 8 Drawing Sheets

U.S. PATENT DOCUMENTS

| | | |
|---|---|---|
| 5,004,468 A | 4/1991 | Atkinson |
| D322,672 S | 12/1991 | Feltovich et al. |
| 5,208,984 A | 5/1993 | Negus |
| 5,219,352 A | 6/1993 | Atkinson |
| 5,342,379 A | 8/1994 | Volinsky |
| 5,386,633 A * | 2/1995 | Kanno .......................... 30/169 |
| 5,595,570 A | 1/1997 | Smith |
| D401,340 S | 11/1998 | Waldman et al. |
| 5,873,881 A | 2/1999 | McEwen et al. |
| 5,921,980 A | 7/1999 | Kirn |
| 6,080,166 A * | 6/2000 | McEwen et al. .............. 606/132 |
| 6,254,619 B1 | 7/2001 | Garabet et al. |
| 6,422,780 B2 | 7/2002 | Chen |
| 6,440,143 B2 | 8/2002 | Kasten |
| 6,530,931 B1 | 3/2003 | Rosenberg |
| 6,540,760 B2 | 4/2003 | Austring et al. |
| 6,663,644 B1 | 12/2003 | Ross et al. |
| 6,702,832 B2 | 3/2004 | Ross et al. |
| 6,923,821 B2 | 8/2005 | Wortrich |
| 6,993,818 B2 | 2/2006 | Smith et al. |
| 7,166,117 B2 | 1/2007 | Hellenkamp |
| 7,166,118 B2 | 1/2007 | Dame et al. |
| 7,175,639 B2 | 2/2007 | Duprat et al. |
| 7,208,000 B2 | 4/2007 | Love |
| 2001/0000833 A1 | 5/2001 | Chen |
| 2001/0047177 A1 | 11/2001 | Kasten |
| 2002/0176754 A1 * | 11/2002 | Barazani ......................... 407/42 |
| 2004/0073246 A1 | 4/2004 | Aufaure et al. |
| 2004/0172045 A1 | 9/2004 | Eriksson et al. |
| 2004/0175690 A1 | 9/2004 | Mishra et al. |
| 2004/0186498 A1 | 9/2004 | Barnes et al. |
| 2004/0225309 A1 | 11/2004 | Eriksson et al. |
| 2004/0230215 A1 | 11/2004 | Eriksson et al. |
| 2004/0243150 A1 | 12/2004 | Werner |
| 2005/0101972 A1 | 5/2005 | Bhatavadekar et al. |
| 2005/0131435 A1 | 6/2005 | Halecki et al. |
| 2005/0234485 A1 | 10/2005 | Seegert et al. |
| 2006/0015124 A1 | 1/2006 | Floerke |
| 2006/0271070 A1 | 11/2006 | Eriksson et al. |

FOREIGN PATENT DOCUMENTS

| | | |
|---|---|---|
| RU | 2086198 | 8/1997 |
| RU | 2294167 | 9/2006 |
| SU | 1184528 | 10/1985 |
| WO | WO99/62412 A1 | 12/1999 |

* cited by examiner

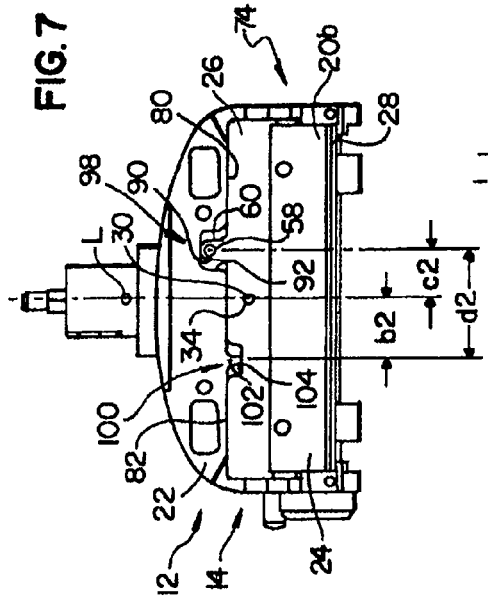

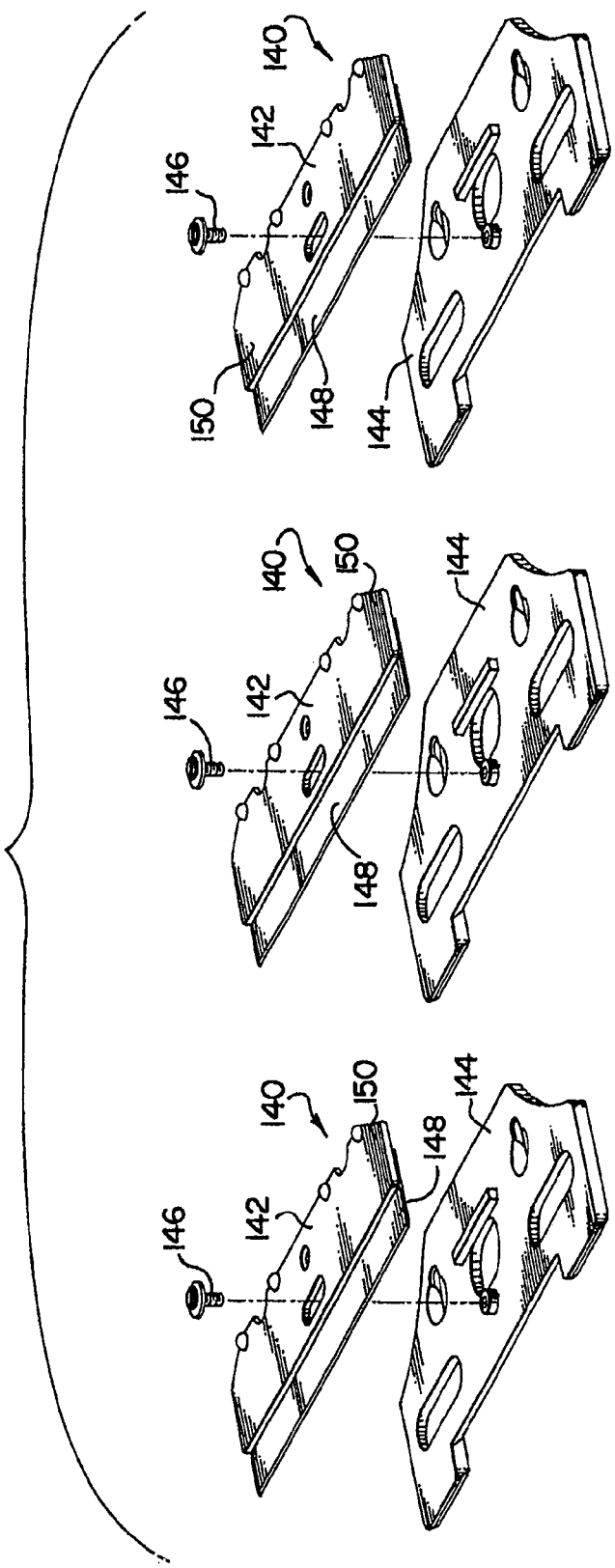

DERMATOME BLADE ASSEMBLY

FIELD OF INVENTION

The present invention relates to dermatomes for surgically harvesting grafts of skin for transplant, and particularly to dermatome blade assemblies.

BACKGROUND

Conventional dermatomes are used for cutting skin tissue to obtain a transplantable skin graft. A skin graft is a patch of healthy skin that is taken from one area of the body or donor site to cover a different damaged or skinless area of the body. Typically, known dermatomes have a head with a flat blade secured to the bottom of the head by a bottom plate. The blade is fixed between the head and the bottom plate with the sharp edge of the blade facing forward. The blade is fixed in a forward and rearward direction while being free to oscillate transversely to create a side-to-side slicing motion for cutting the tissue. The blade is connected to a motor in the device to reciprocate the blade. In use, the dermatome is held so that the blade lies slightly angled relative to the tissue surface to be cut and the blade edge is advanced against the tissue in a direction perpendicular to the direction of oscillation of the blade.

In order to provide a smooth continuous cut that forms straight side edges for the skin graft, the blade must be properly assembled to a dermatome head of an appropriate size. In other words, the width of the blade must match the width of the dermatome head to be used. If the blade is too wide for the dermatome, the lateral ends of the blade will be unsupported and will cause uncontrolled cuts or may cause bending of the blade that increases the dulling of the blade.

Also, blades are sometimes mounted on a carrier which is easier and safer to grasp than the blade and which interconnects the blade to the head of the dermatome and the motor. When the carrier is the same width as the blade, which is often the case, and if the carrier is too large for the dermatome and extends laterally outward beyond the bottom plate with the blade, the contact between the carrier and the skin tissue may cause damage to the tissue.

If the blade is too small, tissue may be pinched between the lateral ends of the bottom plate and the lateral ends of the blade which can lead to rough or jagged edges and a non-continuous cut.

Moreover, if the blade is assembled upside-down on the dermatome, a sharp blade edge having a certain slope relative to the surface of the tissue will be oriented incorrectly and may cause increased dulling of the blade or uneven cuts. Furthermore, some known dermatomes are adjustable to control the thickness of the skin graft. In this case, the known dermatomes have a control bar for being placed on top of a skin tissue surface. The control bar has an adjustable height and has a predetermined range of distances to the blade when the blade is properly assembled on the dermatome. Thus, setting the height of the control bar, sets the depth for the blade under the tissue surface. If the blade is upside-down on the dermatome (where the blade edge still faces forward on the dermatome), the blade may not be set at the expected distance from the control bar. This can occur because either the blade is not properly sitting flush on the dermatome head or the blade is mounted on one side of its carrier (top or bottom) such that mounting the blade and the carrier upside-down places the blade an undesired distance from the control bar. This undesired and unexpected vertical position of the blade can result in undesired skin graft thicknesses.

The known adjustable dermatomes also typically have a lever for shifting the position of the control bar to set the thickness of the skin graft. If the lever is set incorrectly or the switch and/or the control bar are accidentally shifted or bumped, it can result in an incorrect graft thickness. Thus, it would be desirable to have a dermatome that reduces the risk of errors relating to placement of the blade assembly on a dermatome head, and calibration of the dermatome to obtain a desired thickness of the skin graft.

BRIEF DESCRIPTION OF THE DRAWINGS

FIG. 6 is a bottom plan view of a dermatome head of a first size for the dermatome of FIG. 1 and shown without the bottom member;

FIG. 7 is a bottom plan view of a dermatome head of a second size for the dermatome of FIG. 1 and shown without the bottom member;

FIG. 8 is a bottom plan view of a dermatome head of a third size for the dermatome of FIG. 1 and shown without the bottom member;

FIG. 9 is a bottom plan view of an alternative configuration for a dermatome head of the second size and for the dermatome of FIG. 1 and shown without the bottom member;

FIG. 13 is an upper, exploded perspective view of a dermatome head blade assembly kit in accordance with another aspect of the present invention.

DETAILED DESCRIPTION

Figure 1:
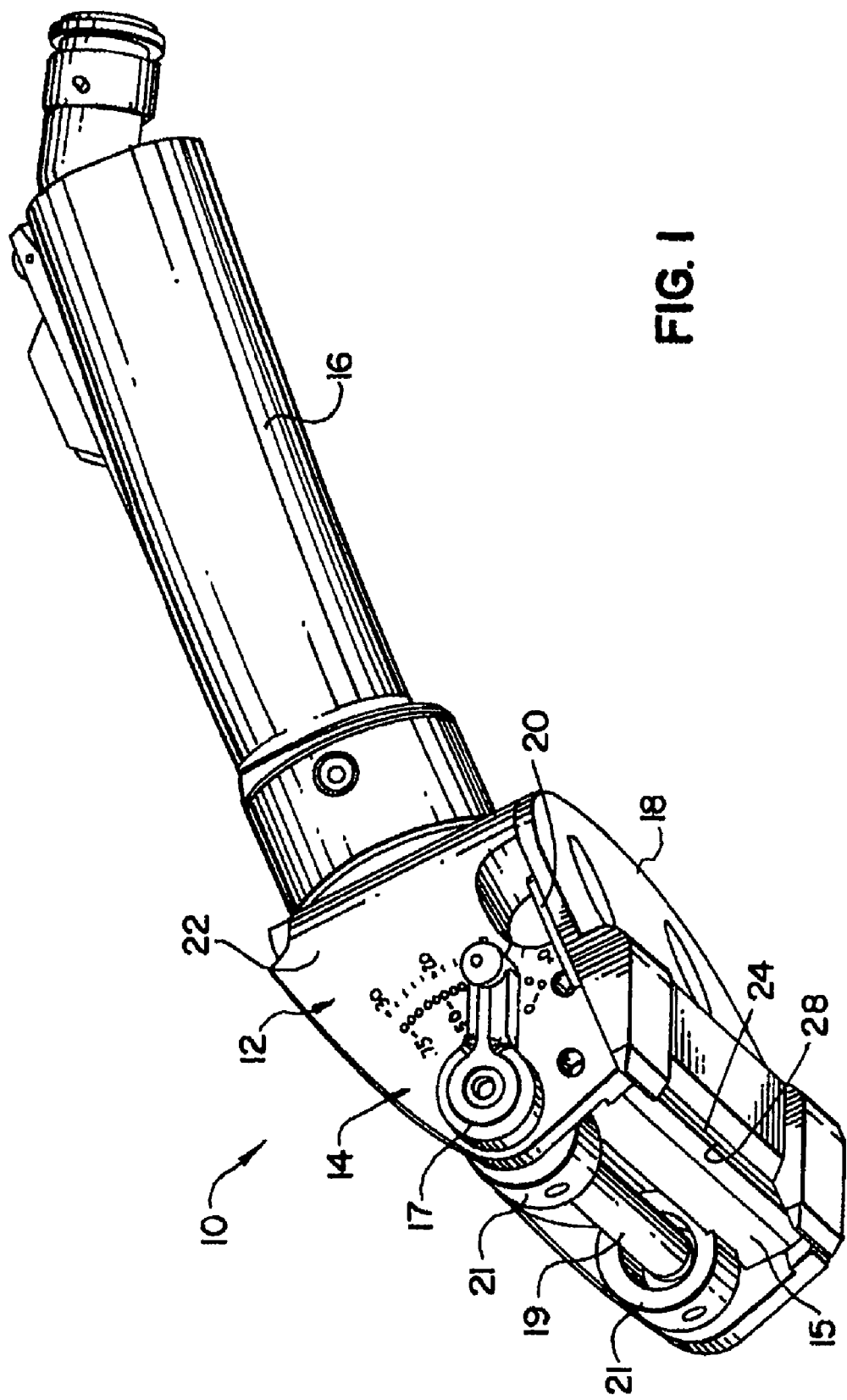
FIG. 1 is a left side perspective view of a dermatome with a head according to the present invention.
Figure 2:
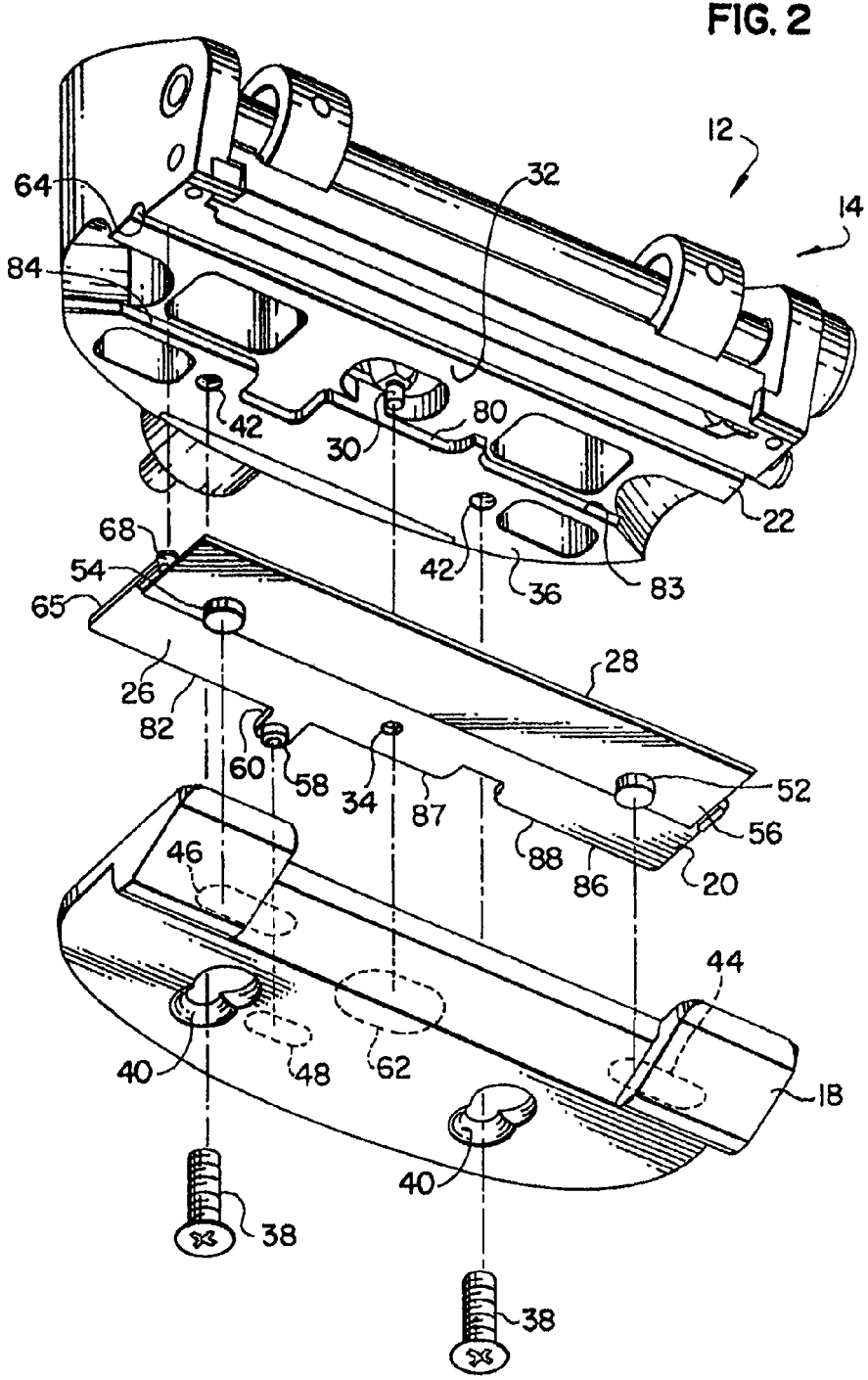
FIG. 2 is an exploded, lower perspective view of the dermatome head of FIG. 1.
Figure 3:
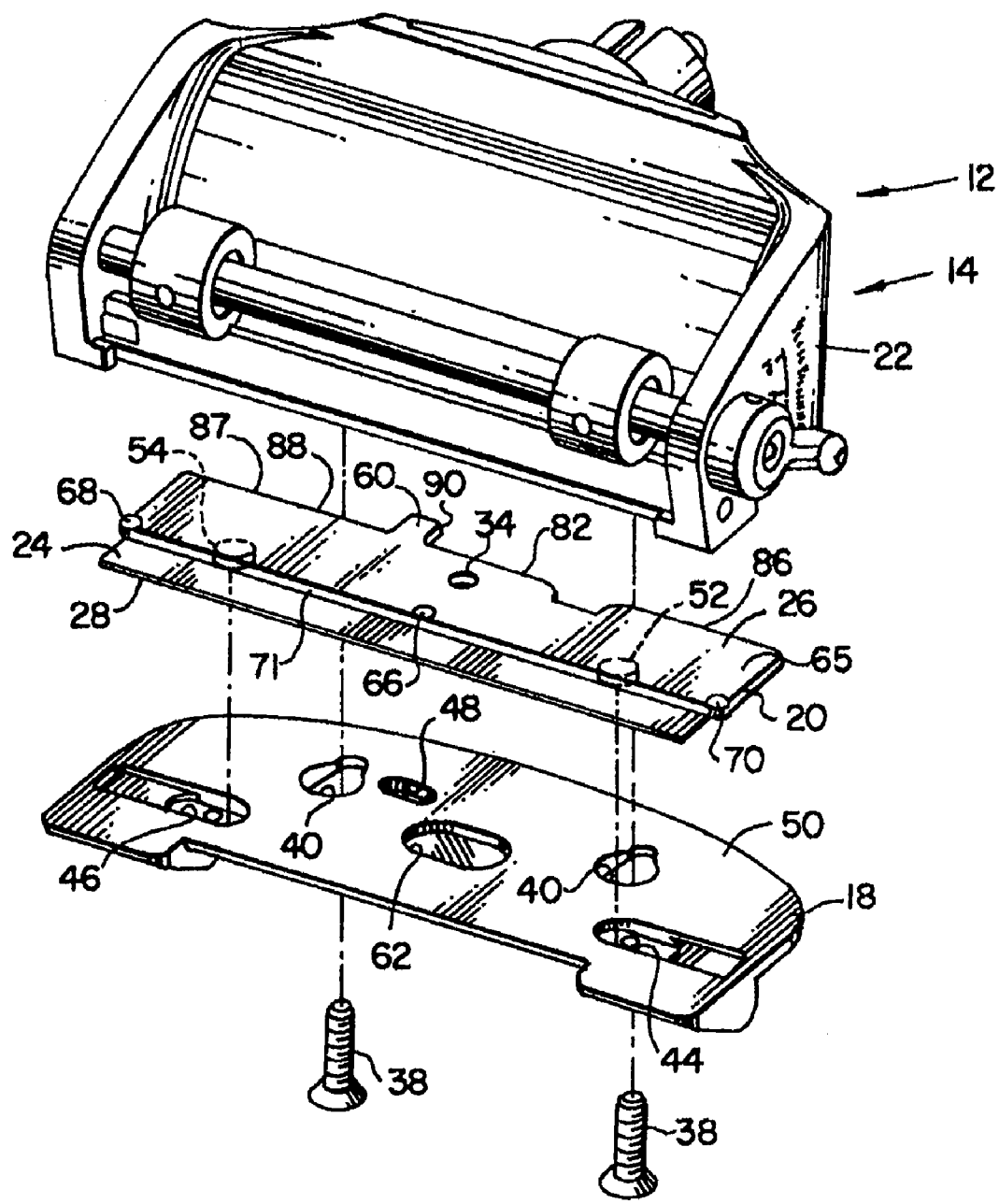
FIG. 3 is an exploded, upper perspective view of the dermatome head of FIG. 1.
Figure 4:
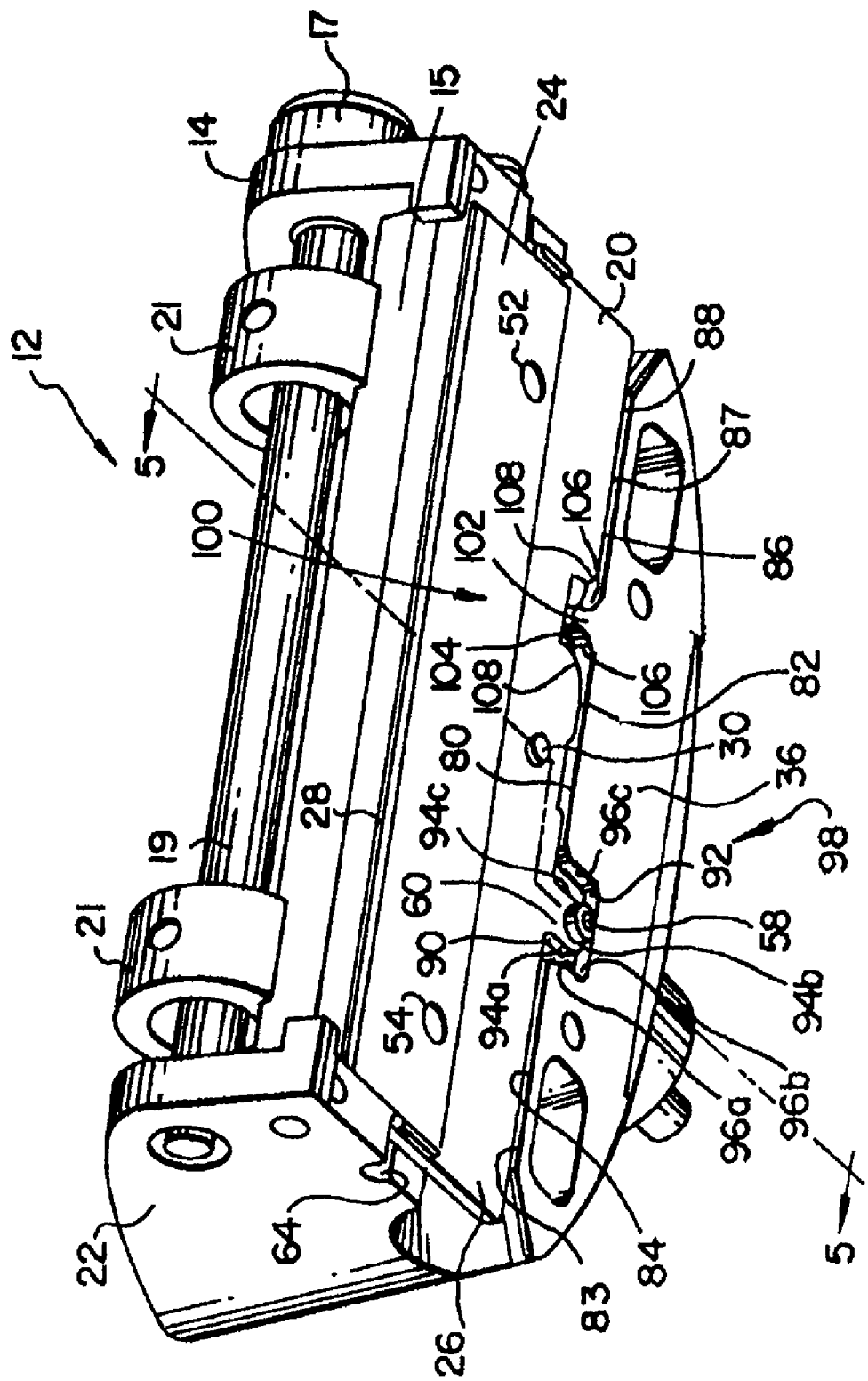
FIG. 4 is a lower, perspective view of the dermatome head of FIG. 1 shown without a bottom member.
Figure 5:
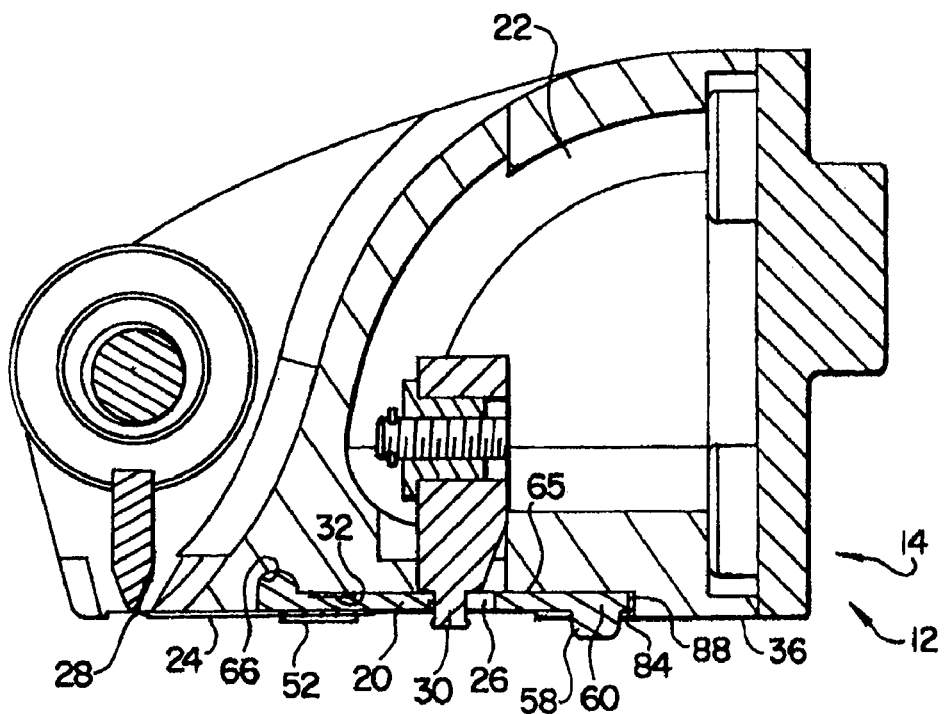
FIG. 5 is a left side cross-sectional view of the dermatome head of FIG. 1.

Referring to FIGS. 1-3, a dermatome 10 for harvesting grafts of skin tissue has a main body 12 with a head 14 connected to a handle 16. The head 14 includes a base member 18 (which also may be a bottom member, bottom plate, or width plate) that secures a blade assembly 20 to a main head portion 22. The blade assembly 20 has a flat blade 24 mounted on a carrier 26 by adhesive, welding or other fasteners, or may be partially embedded within a hard plastic carrier. The blade assembly 20 is disposed on the head 14 so that a front sharp edge 28 of the blade 24 faces forward on the dermatome 10.

The main head portion 22 holds a motor with a reciprocating drive pin 30 that extends out of a lower surface 32 of the main head portion 22. The carrier 26 of the blade assembly 20 lays flush against the lower surface 32 and has an oscillation drive engagement structure 34, such as an opening, for receiving the drive pin 30. This horizontally secures the blade assembly 20 to the drive pin so that transverse oscillation of the drive pin oscillates the blade assembly 20 in a transverse direction forming a side-to-side slicing action on the blade edge 28 (herein the terms horizontal and vertical are used for internal consistency in reference to structure of the dermatome only-horizontal merely refers to a direction generally parallel to a plane generally defined by the flat blade 20 and vertical refers to transverse to the blade plane).

The base member 18 is secured to a dropped surface 36 of the main head portion 22 and that is stepped down from lower surface 32. The base member 18 is secured to the main head portion 22 by screws 38 received by corresponding through-holes 40 on the base member 18 and corresponding bores 42 that open on the dropped surface 36. It will be appreciated that other releasable connectors or attachment mechanisms may be used as long as the base member 18 is able to vertically secure the blade assembly 20 to the main head portion 22 while providing sufficient vertical clearance between the lower surface 32 and the base member 18 to permit the blade assembly 20 to oscillate transversely along with the drive pin 30.

To restrict undesirable longitudinal motion (where the elongate body 12 of the dermatome 10 generally defines a longitudinal direction) and rotational motion of the dermatome about the drive pin 30 which could disrupt the transverse oscillation, the base member 18 has generally transversely extending recesses or slots 44, 46 and 48 on an upper surface 50 of the base member 18 that faces the blade assembly 20. The slots 44 and 46 respectively receive pins 52 and 54 that extend downwardly from a lower surface 56 of the blade assembly 20. The slot 48 receives a pin 58 extending downwardly from a protrusion or tab 60 on the blade assembly 20 and described in greater detail below. The upper surface 50 of the base member 18 also defines a generally transverse recess 62 to provide vertical clearance for the drive pin 30 to oscillate transversely. These pin-slot connections permit the blade assembly 20 to oscillate transversely relative to the base member 18 while fixing the blade assembly 20 in the longitudinal direction and relative to the base member 18.

Likewise, an elongate, transversely extending groove 64 formed on the lower surface 32 receives three (although less or more may be adequate) transversely spaced projections 66, 68, and 70. The projections 66, 68, and 70 extend upwardly from an upper surface 65 of the blade assembly 20, and specifically near a front 71 of the carrier 26, to restrict longitudinal and rotational motion of the blade assembly relative to the main head portion 22 while permitting the projections 66, 68, and 70, and in turn the blade assembly 20, to translate transversely relative to the main head portion 22.

With the configuration described, the blade assembly 20 can be replaced simply by unscrewing threads 38 and removing the base member 18 from the main head portion 22. The blade assembly 20 can then be lifted off of the main head portion 22 for replacement of a dull blade or for disposal after use, for example.

Referring now to FIGS. 4-8, the dermatome head 14 is provided with a certain lateral width (from side to side and perpendicular to the longitudinal direction of the dermatome) that is not substantially greater than the desired width of the skin graft to be cut. Thus, a plurality of dermatome heads such as heads 72, 74, and 76 as shown on FIGS. 6-8, for example, may be available for alternative use where each head has a similar structure to that of head 14 except that each head provides a different width skin graft. In the present example, the heads 72, 74, and 76 respectively provide maximum skin graft widths of about 2, 4, and 6 inches.

On conventional dermatomes, the blade 24 could be mismatched to the head 14 in a number of ways. A practitioner could attempt to load a blade and blade assembly onto a head 14 that does not have a width that corresponds to the width of the head 14. Additionally, the blade assembly 20, and in turn the blade 24, could be placed upside-down on the head 14. To reduce the risk of mismatching the blade 24 and head 14 in the illustrated form, the main body 12 has a profile 80 that has characteristics that correspond to a profile 82 on a blade assembly 20 that has a size (e.g. a width) and an orientation (e.g. right-side up) that corresponds to the main body 12. In other words, the blade assembly 20 cannot be fully loaded onto the main body 12, where the drive pin 30 engages the blade assembly 20, unless the profiles 80 and 82 correspond. Each blade assembly of a different width will have a different profile so that only blade assemblies with a width that corresponds to the width of a head can be fully loaded onto that head. Also, the profiles may have a non-symmetric portion so that if the blade assembly profile 82 is inverted by inverting the blade assembly 20, the inverted profile will not correspond with the profile of the main body 12 either. When the profile characteristics do correspond or align, this indicates that the blade assembly 20 was properly oriented and located for proper mounting on the main body 12. While the profiles 80 and 82 have characteristics that correspond with each other, the profiles are also shaped to provide clearance for the profile 82 on the blade assembly 20 to reciprocate transversely within a predetermined range of motion and relative to the profile 80 on the main body.

In one form, the profile 80 is formed by a thin wall 84 (shown best on FIG. 2) that faces forward on the main head portion 22 and connects lower surface 32 to dropped surface 36. The profile 82 is formed on a rearwardly facing portion 86 of a rim 88 of the blade carrier 26 that opposes the wall 84. It will be appreciated, however, that the profiles 80 and 82 may additionally or alternatively extend on other sides of the blade assembly such as the lateral sides or towards or at the front of the carrier 26 or may even be placed along an enclosed opening within the carrier where a protrusion from the base member 18 and/or main head portion 22 forms the profile 82 within the opening.

Each profile 80 and 82 has at least one contour including a convex contour on one of the profiles 80 or 82 that is received in a concave contour on the other profile 80 or 82. In the present form, one set 98 of corresponding contours includes a convex contour 90 (protrusion or tab 60) of profile 80 that extends rearward from a generally planar surface 87 of the carrier rim 88. The tab 60 is received by a concave contour or groove 92 on the profile 82 of the main head portion 22 and recessed from a generally planar surface 83 of the wall 84. In the illustrated example, the shape of the tab 60 and groove 92 may correspond. Here, the tab 60 is generally square shaped and has three exterior flat sides 94a to 94c (FIG. 4) formed on profile 82 where each side 94 faces a corresponding flat side 96a to 96c of the groove 92 and formed on profile 80.

While the shape of the contours 90 and 92 may correspond, however, the sizes are different to permit the tab 60 to shift transversely within the groove 92. Thus, the groove 92 has a greater transverse width between sides 96a and 96c than the width between sides 94a and 94c on the tab 60 to provide sufficient clearance for the tab 60 to reciprocate through a full transverse range of motion for the oscillation. Middle side 96b of groove 92 is set back from the distal end side 94b of the tab 60 to avoid interference with the end 94b of the tab 60. So configured, the sides 94a-94c of the tab 60 have little, if any, contact with the sides 96a-96c of the groove 92. While the locating pin 58 introduced above extends from tab 60 to engage recess 48 on the base member 18 to restrict longitudinal and rotational motion of the blade assembly 20 as explained above, the pin 58 also helps to ensure that the tab 60 does not jump out of the groove 92 during operation.

Similarly, another set 100 of corresponding contours includes a convex contour or protrusion 102 that extends forwardly from the generally planar surface 87 of the wall 84 and on the profile 80 of the main head portion 22. The protrusion 102 is received in a concave contour or groove 104 recessed from the generally planar surface 83 on the rim 88 and on the profile 82 of the blade assembly 20. The protrusion 102 has concave rounded corners 106 that correspond to convex rounded corners 108. In this case, the groove 104 is reciprocating, and in order to restrict interference with the motion of the groove 104, the protrusion 102 is dimensioned so that little if any contact occurs between the profile 82 at the groove 104 and the profile 80 at the protrusion 102 during operation. It will be understood that the shape of the concave and convex contours 90, 92, 102, and 104 may take on many other forms than that described above.

While in the illustrated form, the profiles 80 and 82 cooperatively form two sets 98 and 100 of corresponding contours, the profiles may have more or less than two sets spaced along the profile, whether or not uniformly spaced. This includes providing a generally curved, jagged, or serrated profile such that surfaces 83 and 87 are no longer generally planar. Thus, the profile may have many different forms as long as the blade assemblies and main head portions have different profiles for different widths and/or to prevent inversion of the blade assemblies.

Referring to FIGS. 6-8, the contour sets 98 and 100 are shown on alternative dermatome heads 72, 74, and 76 with corresponding blade assemblies 20a-20c, respectively. The contour sets 98 and 100 are laterally spaced from each other along the profiles 80 and 82 and at a different predetermined lateral distances d1, d2, or d3, respectively, where each distance corresponds to a predetermined blade width and desired skin graft width. The contour sets 98 and 100 also define distances b1-b3 and c1-c3 to the drive engaging opening 34 so that b1, c1, and d1 are dimensioned for a blade or skin graft width of two inches; b2, c2, and d2 are dimensioned for a 4 inch width; and b3, c3, and d3 are dimensioned for a 6 inch width.

In the illustrated form, the spacing d1-d3 between the contour sets 98 and 100 as well as the distances b1-b3 between the contour set 100 and the opening 34 are different from among heads 72, 74, and 76 depending on the blade width, but the distances c1-c3 between the contour set 98 and the opening 34 remains the same from head to head despite the change in blade width. In another alternative as shown in dash line in FIG. 8, distances b3 and c4 from both contour sets 98 and 100 and to the opening 34 may be different (e.g. b1≠b3, c1≠c4, and d1≠d4) so that all of these dimensions change from head to head depending on the blade width.

As a result of the structure of heads 72, 74, and 76, a blade assembly 20a on the head 72 for a two inch width skin graft cannot be fully assembled on the dermatome heads 74 or 76 for the four and six inch width skin grafts, respectively, because at least one of the lateral dimensions b1 and d1 on the blade assembly 20a do not match the dimensions b2, b3 and d2, d3 on the main head portions 22 of the heads 74 and 76. In other words, when the characteristics of profiles 80 and 82 do not correspond, the protrusion 102 will engage the upper surface 65 of the blade assembly 20 rather than being received in groove 104 when first aligning the drive pin 30 and tab 60 with the opening 34 and groove 92, respectively, to place the blade assembly 20 on the main head portion 22. Similarly, the drive pin 30 will engage the upper surface 65 of the blade assembly 20 and the tab 60 will engage the dropped surface 36 on the main head portion 22 when first aligning the protrusion 102 with the groove 104 to mount the blade assembly 20 to the main head portion 22. In either case, the blade assembly 20 cannot be placed flush against lower surface 32 and cannot engage the drive pin 30 for reciprocation.

In yet another alternative configuration for the profile contours as shown in FIG. 9, a head 78 has the same spacing between contour sets 98 and 100 as the head 74 (d2=d5), but the distances b5 and c5 from the contour sets 98 and 100 to the opening 34 are different from the distances b2 and c2 on the head 74. In this case, the distance or spacing d5 between contour sets 98 and 100 is still the same as d1, but the lateral position of the contour sets 98 and 100 along the profiles 80 and 82 are changed relative to a longitudinal axis L of the head 78. Thus, maintaining the same spacing between two or more contour sets from head to head and transversely shifting the location of the contours along the profile also will obtain the same result: a blade assembly 20d that fits on head 78 cannot be fully assembled to the heads 72, 74, and 76.

In a further alternative configuration, instead of changing the location of the contour sets 98 and 100, the shape (including the size) of the contours may be changed from head to head with different blade widths to obtain the desired profile relationships. Thus, alternative contour sets 99 and 101 (shown in dashed line on FIG. 9) have larger outer dimensions with the same shapes than that of contour sets 98 and 100 such that a blade assembly with a profile with these larger contours will not have characteristics that correspond with the profiles of heads 72, 74, and 76, for example, and cannot be fully mounted on those heads.

Similar results occur when the blade assembly 20 is inverted (about a longitudinal axis L shown on FIGS. 6-9 of the dermatome and head so that the blade edge 28 still faces forward). In this case, no clearance exists to place the blade assembly 20 flush against the lower surface 32. More specifically, when the blade assembly 20 is inverted, the pin 58 extending from tab 60 will engage the dropped surface 36 so that the blade assembly 20 cannot lay flush against lower surface 32. This results in the blade assembly 20 spanning over lower surface 32 such that the drive pin 30 cannot be operatively disposed in the drive engaging structure opening 34 on the blade assembly 20 to reciprocate the blade and blade assembly.

It will be understood that a practitioner may be supplied with a number of dermatomes (or a number of dermatome heads mountable on the same handle 16), where each dermatome or dermatome head is configured to cut a different skin graft width. A supply of blade assemblies also may be provided that also are configured to provide a plurality of different skin graft widths. In this case, each blade assembly will have a profile that corresponds to a blade or skin graft width and that has corresponding characteristics to a profile on a dermatome head for cutting the same skin graft width. The blade assembly can only be fully mounted on the dermatome with the corresponding profile. As mentioned above, the profiles may have contours on different locations along the profile or contours with different shapes depending on the width of the skin graft.

Referring again to FIGS. 1 and 4, the head 14 has an adjustable control bar 15 that is operated by rotating a handle or switch 17, which rotates a member 19 and cams 21 on the control bar 15. The cams 21 engage the control bar 15 so that rotating the cams 21 causes the control bar 15 to move up and down and closer and farther from the sharp blade edge 28 as desired. The control bar 15 is placed against the skin tissue and the blade cuts into and under the tissue surface so that the cut skin tissue moves between the control bar 15 and the blade 20 and up and over the main head portion 22.

Figure 10:
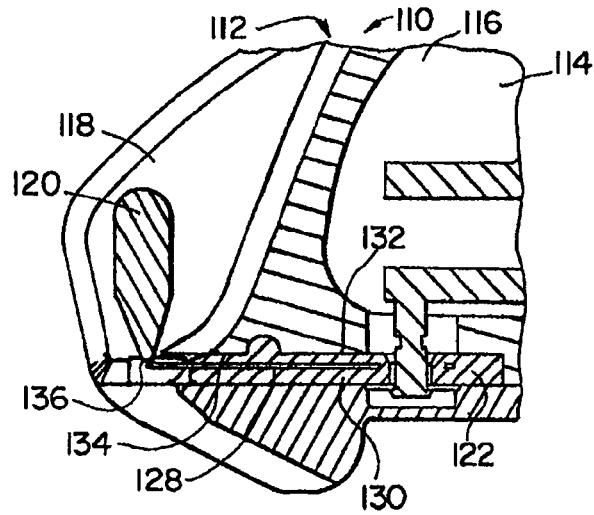
FIG. 10 is a left side, cross-sectional-view of an alternative dermatome head according to another aspect of the present invention and configured with a first alternative blade assembly.
Figure 11:
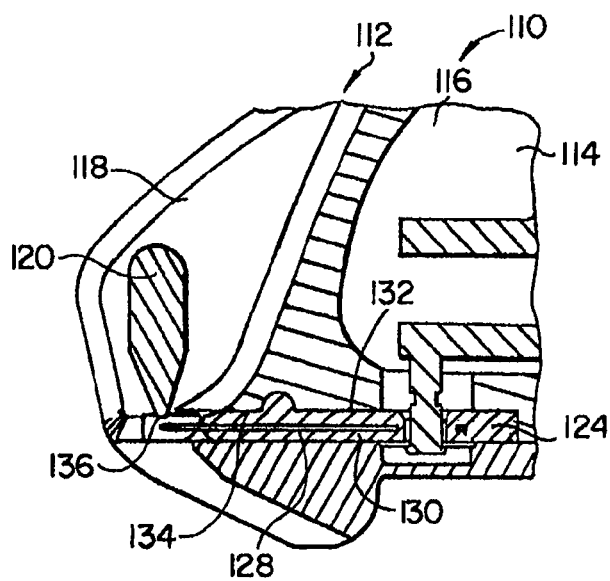
FIG. 11 is a left side, cross-sectional-view of the alternative dermatome head of FIG. 10 and configured with a second alternative blade assembly.
Figure 12:
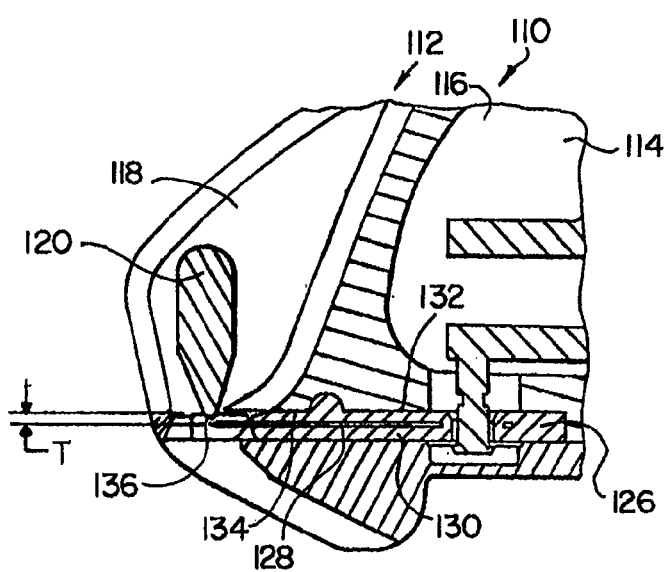
FIG. 12 is a left side, cross-sectional-view of the alternative dermatome head of FIG. 10 and configured with a third alternative blade assembly.

Referring now to FIGS. 10-12, in contrast to the control bar 15, a dermatome 110 has a main body 112 with a non-adjustable head 114. The head 114 has a main head portion 116 has a front section 118 that supports a transversely extending, elongate, fixed control bar 120 for engaging a tissue surface to be cut for a skin graft. Otherwise, the features of the head 114 are the same or similar as those provided on head 14 described above and are numbered similarly. Here, however, the main body 112, or more specifically the main head portion 116, alternatively receives one of a plurality of interchangeable blade assemblies 122, 124, and 126. Each blade assembly 122, 124, and 126 is configured to provide a skin graft of a different thickness.

Each blade assembly 122, 124, 126 has a blade 128 mounted on a carrier 130. The blade assemblies 122, 124, and 126 each have an outer surface 132 that is configured to engage, or lay flush against, a lower surface 134 of the main head portion 116. In one form, the outer surface 132 is formed by the carrier 130. The blade 128 on each blade assembly 122, 124, and 126 is disposed at a different distance from the outer surface 132 on each blade assembly which corresponds to a desired skin graft thickness.

The control bar 120 has a lower control surface 136 for contacting tissue and is spaced from the blades 128 at predetermined distances t (shown for example on FIG. 12), that correspond to the desired skin graft thicknesses. Thus, the skin graft thickness is set depending on the distance between the blade 128 and the outer surface 132. In one example, the distance t=0.030 inches for blade assembly 126, t=0.015 inches for blade assembly 124, and t=0.0 inches for blade assembly 122 (the t=0.0 inch example is provided here merely to show the blade can be set at a desired depth close to 0).

This configuration substantially eliminates the risk of an adjustable control bar being unintentionally set at an undesirable distance from the blade 128. It will be appreciated, however, that while the control bar 120 is described as being fixed, a control bar could be optionally fixed so that the head 114 can alternatively accept the interchangeable blade assemblies 122, 124, or 126 preset for a specific skin graft thickness, or blade assembles, such as blade assembly 20, with a uniform blade position on the carrier to be used with an adjustable control bar. In such a case, the head would provide a switch for selecting between an adjustable control bar mode and a fixed control bar mode.

It will also be appreciated that while three interchangeable blade assemblies are shown corresponding to three different skin graft thicknesses, the blade assemblies are not so limited and any number of blade assemblies may be provided to obtain any number of different desired corresponding skin graft thicknesses.

Referring to FIG. 13, a kit 138 has a plurality of partial dermatome head kit assemblies 140 formed with a plurality of blade assemblies 142 and a plurality of base members 144. Each kit assembly 140 has at least one of the blade assemblies 142 releasably secured to, and preassembled with, at least one base member 144 by a screw 146 or other releasable fastener or adhesive. The screw 146 fits through an opening 148 on the blade assembly 142 and into a bore 150 on the base member 144. The blade assembly 142 may have a blade 148 mounted on a carrier 150 as with any of the blade assemblies described herein. Each base member 144 is configured to alternatively and releasably secure the blade assembly 142 to a main head portion, such as a main head portion 22 or 118 described above, or other similar dermatome heads. This reduces the risk of mismatching a blade assembly to a base member that does not have a corresponding width as that of the blade assembly. The screw 146 is removed when mounting the kit assembly 140 to a main head portion.

In one form, a number of the blade assemblies 142 cut a different skin graft width relative to each other so that a number of the kit assemblies 140 correspond to a variety of desired skin graft widths. Alternatively or additionally, a number of the blade assemblies 142 may be configured to cut different skin graft thicknesses relative to each other such that a number of the kit assemblies 140 correspond to a variety of desired skin graft thicknesses.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

What is claimed is:

1. A dermatome comprising:
a main body having a first profile and a longitudinal axis; and
at least one blade assembly generally lying in a plane and comprising
a blade,
a size,
a non-inverted orientation corresponding to the main body,
a second profile having characteristics corresponding to the first profile to properly orient and locate the at least one blade assembly for proper mounting to the main body,
an outer back surface extending transverse to the plane and forming the second profile wherein only the outer back surface forms the second profile, and
at least two contours spaced along the outer back surface and forming part of the outer back surface as a portion of the second profile, the contours extending with the plane,
wherein the blade assembly will not mount to the main body unless the size or non-inverted orientation corresponds to the main body,
wherein the profiles are shaped to provide clearance for the second profile to reciprocate in a lateral direction relative to the longitudinal axis and in relation to the first profile,
wherein the first profile has contours corresponding to the contours of the second profile and including a convex contour on one of the profiles that is received in a concave contour on the other profile, and wherein the blade assembly cannot be mounted on the main body for use unless the first and second profiles are generally aligned with each other;
further comprising at least two sets of corresponding contours wherein the sets are spaced from each other along the profiles and in opposite configurations so that each profile has at least a concave contour spaced from a convex contour.

2. A dermatome of claim 1 wherein the sets are spaced from each other along the profiles at a predetermined distance.

3. The dermatome of claim 2 wherein a predetermined size blade corresponds to the predetermined distance.

4. The dermatome of claim 1, wherein the blade further comprises an oscillation drive engaging structure disposed on the blade a predetermined distance from the at least one contour.

5. The dermatome of claim 1 further comprising a plurality of blade assemblies including the at least one blade assembly, the plurality of blade assemblies providing a plurality of widths and a plurality of profiles, each width corresponding to a different profile, and wherein only the blade assemblies with the second profile with the characteristics corresponding to the first profile are configured to be fully assembled on the dermatome.

6. The dermatome of claim 5 wherein the contours are located on different positions along the profile depending on the width of the blade assembly, and wherein the contours of the first and second profiles correspond depending on the location of the contours along the profile.

7. The dermatome of claim 5 wherein the contours have different shapes depending on the width of the blade assembly, and wherein the first and second profiles correspond depending on the shape of the contours.

8. A dermatome of claim 1, wherein the blade assembly has a rim forming the second profile, and wherein the main body has a wall forming the first profile and facing the rim.

9. The dermatome of claim 1 wherein one of the first and second profiles has a protrusion, and the other of the first and second profiles has a groove for receiving the protrusion, and wherein the groove is sized to permit the protrusion to reciprocate within the groove.

10. A dermatome of claim 1 wherein the profiles are configured so that only a blade assembly holding a blade of a predetermined width can be fully assembled on the dermatome.

11. A dermatome of claim 1 wherein the profiles are configured so that the blade assembly cannot be assembled to the main body in an inverted orientation.

12. The dermatome of claim 1 wherein the blade assembly has an outermost rim, and wherein the second profile forms a portion of the outer most rim.

13. The dermatome of claim 1 wherein the first and second profiles are non-symmetric in the lateral direction about the longitudinal axis.

14. The dermatome of claim 1 wherein the main body generally defines a longitudinal axis and comprises a transverse wall forming the first profile, and wherein the contours extend from the wall in an axial direction relative to the axis.

15. The dermatome of claim 1 wherein the at least two contours are separated along the second profile by a flat, linear portion of the back surface wall.

* * * * *